US006284289B1

(12) United States Patent
Van den Berghe

(10) Patent No.: US 6,284,289 B1
(45) Date of Patent: *Sep. 4, 2001

(54) TREATMENT OF HERPES INFECTION WITH COMPOSITION CONTAINING QUATERNARY AMMONIUM COMPOUND AND AN ANTI-VIRAL AGENT

(75) Inventor: Dirk Andre Richard Van den Berghe, Laarne (BE)

(73) Assignee: Bio Pharma Sciences B.V. (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/875,661
(22) PCT Filed: Jan. 23, 1996
(86) PCT No.: PCT/NL96/00038
   § 371 Date: Nov. 5, 1997
   § 102(e) Date: Nov. 5, 1997
(87) PCT Pub. No.: WO96/24367
   PCT Pub. Date: Aug. 15, 1996

(30) Foreign Application Priority Data

Feb. 6, 1995 (NL) ..................................... 9500216

(51) Int. Cl.[7] ........................... A61K 35/78; A01N 33/12; A01N 37/02
(52) U.S. Cl. ........................... 424/746; 514/544; 514/643
(58) Field of Search ........................... 424/195.1, 746; 514/544, 643

(56) References Cited

U.S. PATENT DOCUMENTS

| | | | |
|---|---|---|---|
| 4,053,628 | * 10/1977 | Stevenson et al. | 514/456 |
| 4,478,818 | * 10/1984 | Shell et al. | 424/14 |
| 4,548,950 | * 10/1985 | Baxendale et al. | 514/510 |
| 4,895,727 | * 1/1990 | Allen | 424/642 |
| 4,902,720 | * 2/1990 | Baldone | 514/642 |
| 4,943,433 | * 7/1990 | Rudov | 424/195.1 |
| 5,387,611 | * 2/1995 | Rubinstein | 514/588 |
| 5,443,840 | * 8/1995 | Morancais et al. | 424/450 |
| 5,455,033 | * 10/1995 | Silverman et al. | 424/195.1 |

FOREIGN PATENT DOCUMENTS 0308210   3/1989  (EP).

04005206  * 1/1992  (JP).

OTHER PUBLICATIONS

Colegate, Steven M. et al., "Antiviral Agents from Higher Plants and an Example of Structure–Activiey Relationship of 3–Methoxyflavones," BioActive Natural Products: detection, isolation, and structural determination, 405–440. CRC Press, Inc. 1993.

Vanden Berghe, D. A., et al., "Screening Methods for Antibacterial and Antiviral Agents from Higher Plants," Methods in Plant Biochemistry, vol. 6, pp. 47–69, 1991.

Dauphin, A. et al., "Hygiène Hospitalière Pratique," Sous l'égide de l'APHIF Association de Pharmacie Hospitalière de l'Ile–de–France, 2nd Edition, 16 pp.

Kurokawa, M. et al., "Efficacy of traditional herbal medicines in combination with acyclovir against herpes simplex virus type 1 infection in vitro and in vivo," Antivir. Res., vol. 27., No. 1–2, pp. 19–37, 1995.

Amoros, M. et al., "Effect of saponins from *Anagallis arvensis* on experimental herpes simplex keratitis in rabbits," Planta Med., vol. 54, No. 2, pp. 128–131, 1988.

Sands, J. A. et al., "Virucidal activity of cetyltrimethylammonium bromide below the critical micelle concentration," Fems Microbiol. Lett., vol. 36, No. 2–3, pp. 261–263, 1986.

Damery, B. et al., "Virucidal activity against herpes and vaccinia virus of 8 antiseptic formulations," Int. J. Pharm., vol. 49, No. 3, pp. 205–208, 1989.

Suganda et al., J. Nat. Prod. (LLoydia), 1983, 46(5), 626–632, 1983.*

Baba et al. "Antiviral activity of glycyrrhizin against varicella–zoster virus in vitro," Antiviral Res. (1987) 7: 99–107; 1987.*

* cited by examiner

Primary Examiner—David M. Naff
Assistant Examiner—Mike Meller
(74) Attorney, Agent, or Firm—Webb Ziesenheim Logsdon Orkin & Hanson, P.C.

(57) ABSTRACT

A pharmaceutical composition and method for the treatment of herpes simplex infections is disclosed. The composition contains a quaternary ammonium compound such as cetrimide or benzalkonium chloride and an antiviral agent such as acyclovir, bromoinyldesoxuridine, 3-fluorothymidine, idoxuridine, propyl gallate, proanthocyanides or glucosamine. The compound can also contain a plant extract such as camomile.

10 Claims, No Drawings

TREATMENT OF HERPES INFECTION WITH COMPOSITION CONTAINING QUATERNARY AMMONIUM COMPOUND AND AN ANTI-VIRAL AGENT

The present invention relates to a pharmaceutical composition for the treatment of herpes.

Herpes simplex infection on the skin causes superficial painful spots and blisters, which eventually open, thereby causing lesions. Herpes is mainly caused by Herpes simplex virus (HSV) type 1, but can also be the result of HSV type 2 which usually causes genital herpes. Conversely, genital herpes is caused in about 30% of cases by HSV 1.

Infections of the mouth are designated with the term herpes labialis, also called cold sore (feverblister). Other parts of the face, such as eyes and nose, can also be affected. This is then referred to as facial herpes simplex. The infection can also manifest itself on other parts of the body.

About 70–90% of the population is primarily infected with HSV. These people are then carriers of the virus. Once an individual has been infected with the HSV, this virus will thereafter remain latently present in the body. In latent state the virus is situated in nerve cell bodies in the ganglia. Due to particular stimuli, such as influenza infection or other respiratory disorders, gastro-intestinal infections, stress, fatigue, menstruation, pregnancy, allergy, sunlight and fever, the latent virus can be activated. It will travel from the ganglia along well-defined nerve paths to the skin surface and there multiply and cause the symptoms. This recurrent form of herpes occurs in about 40% of the infected individuals.

A per se reasonably innocuous herpes simplex infection can lead to much more serious infections, such as keratitis and encephalitis. It is therefore important that the virus niduses, at the location of the infection, are efficiently destroyed.

At the moment the most frequently used remedy against HSV infections is acyclovir, which is sold for instance under the brand name Zovirax. Acyclovir is a guanine analog which interferes with the DNA polymerase of the virus and thereby inhibits viral DNA replication. The virus is prevented from multiplying but the virus itself is however not killed. The virus can therefore withdraw to the ganglia, thus resulting once again in latency.

Transmission of HSV-1 occurs through direct contact via saliva or the infected spot on the skin. This transmission is also not prevented by acyclovir.

Another problem is the occurrence of secondary bacterial infections, for instance impetigo, caused by staphylococci and/or streptococci.

On account of these problems of herpes infection, which may or may not be attendant, there is an obvious need for a pharmaceutical preparation which can diminish or even prevent the occurrence of latency as well as the transmission and secondary bacterial infections.

According to the present invention it has now been found that a pharmaceutical composition consisting of a quaternary ammonium compound as a first component and/or an anti-viral agent as a second component and/or a plant extract as a third component, wherein the three components are mutually compatible, in a pharmaceutically acceptable base, can resolve the above stated problems.

In order to break the vicious circle of latency, recurrence and renewed latency of the virus, it is necessary to kill the virus itself. Less or even no latency can hereby reoccur in the case of primary or recurrent infection since the dead virus cannot withdraw into the ganglia. The most important component of the present composition according to the invention is therefore a virucidal substance whereby the virus is killed.

Antiviral agents can be subdivided into a number of categories (Colgate, S. M. & Molyneux, R. J., Bio-active natural products, 410, CRC Press, Inc. (1993)), designated with the classification group Ia to group Vb. According to the invention it has now been found that, in order to deal with HSV infections to the fullest possible extent, preferably one or more substances from group IVb must be combined with one or more substances from group Va. Substances from group IVb exhibit virucidal activity, while compounds from group Va display virustatic and antiviral activity. By the combination of both types of substance the virus replication is inhibited and in addition the viruses already present are killed.

In order to ensure that the secondary infection of the lesion caused by HSV infection by other micro-organisms such as bacteria is prevented, it is recommended that either the first component and/or the second component has disinfecting properties.

In order to alleviate the associated symptoms of pain and inflammation a plant extract is preferably also used. This extract preferably also has a soothing effect in addition to inflammation-inhibiting properties.

Products from group IVb which also have a disinfecting activity and can therefore be used in the pharmaceutical composition according to the invention can be selected in a manner known to the skilled person. Use is herein made of the end point titration technique (EPTT) as described by Colgate & Molyneux (supra. p. 413), with which the virucidal activity of a product can be tested. The activity is expressed in virus titre reduction which is determined in vitro by incubation of a herpes virus suspension with dilutions of the product for testing at 37° C. for 5 minutes. A good product will give a minimal titre reduction of $10^3$.

From a general screening of known disinfectants for their virucidal action against Herpes simplex type 1 and Herpes simplex type 2 strains (clinical isolates) it has been found according to the invention that a few products display very high activity, even at 25° C. This is very advantageous because the temperature on the skin is generally lower than 37° C. and even lower than 34° C. It has been found that the quaternary ammonium compounds cetrimide and benzalkonium chloride in a concentration of 50–200 $\mu$g/ml and 100–200 $\mu$g/ml respectively showed a titre reduction of at least $10^3$ for a test period of 5 minutes at 25° C. Other known disinfectants, such as alcohols, phenols, peroxides, biguanides, aldehydes, chlorine compounds etc. displayed an activity which was a minimum of five times lower. Only mercury compounds and determined heavy metal compounds have a better activity. However, due to their high toxicity these compounds are not suitable for the intended application.

All quaternary ammonium compounds can in principle be used with the general formula:

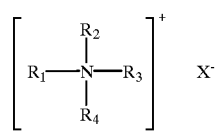

wherein $R_1$, $R_2$, $R_3$, and $R_4$ can be the same or different and represent an aliphatic or aromatic group, wherein at least one of $R_1$, $R_2$, $R_3$ or $R_4$ is an aliphatic chain of 8 or more carbon atoms; and wherein X is a low molecular weight inorganic anion or a high molecular weight organic anion. A survey of suitable quaternary ammonium compounds is given for instance by A. Dauphin & J. C. Darbord in "Hygiène hospitalière pratique", Editions medicales internationales, Paris (1988). Cetrimide is highly recommended.

Quaternary ammonium compounds are well soluble in water and alcohol but cannot be combined with any random other product. An important requirement for the second component is therefore that it must be compatible with the first component. Anionic products, soaps, nitrates, heavy metals, oxidizing products, rubber, proteins and the like are not compatible with quaternary ammonium compounds. Such products are therefore not suitable for use in the composition according to the invention. The second component is preferably not teratogenic and can be given in a high dosage without being toxic therein. In preference the second component further shows a good penetration of the skin.

As second component known antiviral products can be used, such as acyclovir, BVDU, 3FT, Idoxuridine etc., as long as they are compatible with the first component. In addition non-toxic natural products with antiviral activity can be used.

The suitability of the second component can likewise be tested with a per se known EPTT method (Colgate & Molyneux, supra, p. 414). Use is herein made of VERO cells. According to the invention it has thus been found that gallates have a good antiviral activity in vitro. Propyl gallate in a concentration of 100 µg/ml thus has a titre reduction factor of $10^4$. In a concentration of 25 µg/ml the reduction factor of the infectious particles in VERO cells is $10^3$. Ethyl gallate has a reduction factor of $10^4$ in a concentration of 100 µg/ml and of $10^2$ at 25 µg/ml. Ethyl gallate is therefore slightly less active.

The compatibility of the first component and the second component can be determined by testing a mixture of the two components on HSV-1. It has been found that a mixture of propyl gallate and cetrimide (2:1) in a concentration of 250 µg propyl gallate to 125 µg cetrimide still has a virucidal action of $10^3$ after a test period of 5 minutes at 25° C. The same applies in the case of ethyl gallate and cetrimide. A mixture of cetrimide and BVDU or acyclovir continues to display an antiviral activity after dilution in vitro to 5 µg/ml BVDU or. acyclovir and 0.1 µg/ml cetrimide.

The pharmaceutical composition preferably also contains a plant extract, with which the pain and effects of the inflammation reaction can be alleviated. Here it is also the case that the extract may not interfere with the activity of the first and the second component.

For this purpose various plant extracts were tested with cetrimide and propyl gallate or benzalkonium chloride and propyl gallate to see whether the virucidal activity is maintained and the components are compatible. It has been found that extracts of camomile and Calendula remain useable in vitro. Extracts of Aloe vera, Echinaceae root, tricolor violet, Senna, Melissa and/or hawthorn are also capable of alleviating the inflammation reaction or pain while the virucidal activity is retained.

Particular plant extracts however cause a marked reduction in the virucidal activity of some quaternary ammonium compounds. It has for instance been found that 10% hamamelis completely deactivates the virucidal and antibacterial activity of benzalkonium chloride (0.5%). The activity of 0.1% benzalkonium chloride against herpes and bacteria is reduced 4 to 8 times by sage and great burdock extract. However, a combination of cetrimide with a second component and a plant extract of camomile, Calendula, sage, great burdock and senna was found in vitro to remain active against Herpes simplex virus as well as bacteria.

The compatibility of the plant extract to be used must therefore be determined beforehand. Such a determination lies within the reach of the average skilled person.

Suitable plant extracts come for instance from *Aesculus hippocastanum* L; *Aloe vera* L; *Anagallis arvensis* L; *Anthemis nobilis* L; *Arctium lappa* L; *Aristolochia clematitis* L; *Arnica montana* L; *Betonica officinalis* L; *Calendula officinalis* L; *Capsicum annuum (tetragonum)*; *Carica papaya* L; *Carlina acaulis* L; *Caryophyllus aromaticus* L; *Cynoalossum officinale* L; *Echinacea anaustifolia*; *Echinacea purpurea* L; *Eupatorium cannabinum* L; *Geranium robertianum*; *Geum urbanum* L; *Glechoma hederacea* L; *Hamamelis virginiana* L; *Hypericum perforatum* L; *Inula helenium* L; *Jualans regia* L; *Juniperus oxycedrus* L; *Lavandula officinalis*; *Lawsonia alba* L; *Lysimachia nummeralia* L; *Lythrum salicaria* L; *Malva sylvestris*; *Marrubium vulgare* L; *Matricaria chamomilla* L; *Mentha piperita* L; *Myroxylon balsamum* L; *Myrtus communis* L; *Olea europaea* L; *Prunus amyadalus*; *Pyrus cydonia* L; *Quercus robur* L; *Quillaja saponaria*; *Rubus idaeus* L; *Salvia officinalis* L; *Saponaria officinalis* L; *Smilax officinalis*; *Solanum dulcamara* L; *Solidago virga aurea* L; *Styrax tonkinensis*; *Styrax benzoides*; *Styrax benzoin*; *Symphytum officinale* L; *Trigonella foenum-graecum* L; *Tropaeolum majus* L; *Urtica urens* L; *Urtica dioica* L; *Viola tricolor* L.

The pharmaceutical composition according to the invention, which consists of a combination of one or more quaternary ammonium compounds with a virucidal and antiseptic activity and/or an antiviral product which is compatible with the quaternary ammonium compound and inhibits the virus replication, and/or a plant extract which is likewise compatible with both above mentioned products and alleviates the associated effects of the herpes infection such as pain, itching, swelling, tingling etc., provides a total treatment of herpes infection. The virucidal activity of the composition kills the viruses, whereby latency will occur less or not at all. The antiviral activity inhibits the virus replication and therewith the multiplying of the virus. The antiseptic activity prevents secondary bacterial infections. Finally, the inflammation-inhibiting activity prevents inflammation and moreover soothes the pain and the itching.

The components of the composition according to the invention are preferably included in a pharmaceutically acceptable base. For the base also applies that it may not reduce the activity of the three components. In order to test whether a base is suitable, the virucidal activity of the first component and the disinfecting activity can be determined. The disinfecting activity is for instance determined in a manner lying within reach of the skilled person for a period of 5 minutes at 25° C. on Gram-negative germs, for instance of *Pseudomonas aeruainosa* or *Escherichia coli*.

Examples of suitable bases are polyethylene glycols in different molecular sizes or mixtures thereof, esters of fatty acids or mixtures thereof, whether or not mixed with emulsifying and/or skin-care constituents. Also suitable are mixtures of polyethylene glycols and/or esters of fatty acids with or without the emulsifying and/or skin-care constituents.

The pharmaceutical composition according to the invention can take the form of a powder, suspension, solution, spray, emulsion, unguent or cream and can be used for localized application. Such composition can be prepared by combining (i.e. mixing, dissolving etc.) the active components in the form of a free acid or salt with pharmaceutically acceptable excipients of a neutral character (such as aqueous or non-aqueous solvents, stabilizers, emulsifiers, detergents, additives) and in addition, where necessary, colorants, aromatic substances and/or flavourings. The concentration of the active ingredient(s) in a pharmaceutical composition can vary between 0.001% and 100% (w/v), depending on the nature of the treatment and the manner of application. An unguent is recommended.

The composition of the invention contains for instance 10–90% of a non-aqueous base, 1–20% of an alcohol, 0.1–5% of one or more quaternary ammonium compounds, and/or 0.01–2% of one or more Antiviral agents, and/or 0.5–10% of one or more plant extracts. The quantity of plant extract used is closely related to the activity thereof and to the concentration of active constituents in the extract.

A preferred composition according to the invention contains 20–60%, preferably 52% PEG 400, 10–40%, preferably 26% PEG 4000, 2–20%, preferably 9% glycerol, 0.5–1.8%, preferably 1% cetrimide, 0.2–3%, preferably 1% cetyl alcohol, 5–15%, preferably 8% camomile extract and 0.2–1%, preferably 0.25% propyl gallate.

The present invention will be further elucidated with reference to the accompanying examples, which are however not intended to limit the invention in any way whatever.

EXAMPLES

Example 1

I. Preparation of the Anti-herpes Preparation
With the following ingredients:

| | | |
|---|---|---|
| A. | Polyethylene glycol 400 | 52% |
| | Polyethylene glycol 4000 | 26% |
| | Glycerol | 9% |
| | Cetrimide | 1% |
| | Choline chloride (optional) | 2% |
| | Cetyl alcohol | 1% |
| B. | Camomile extract | 8% |
| | Propyl gallate | 1% | an unguent was prepared by melting the ingredients under A at 75° C. and dissolving the ingredients under B. The mixture of the ingredients under A obtained after melting was subsequently mixed homogeneously while being cooled slowly and the mixture of B was added before solidifying of the mixture of A. Mixing was then continued until the total mixture was fully cooled. The mixture was named 93J12.

Polyethylene glycol 400 and 4000 were obtained from Pharmaceuticals, which markets them under the trade names Macrogol 400 - Purna and Macrogol 4000. Glycerol was of p.a. quality and came from Merck (4094), cetrimide A 11936 was supplied by Pharmachemic NV, choline chloride (C1879) by Sigma. Cetyl alcohol is marketed under the brand name Lanette 16 by Henkel KGaA. The liquid camomile extract came from Conforma and propyl gallate P3130 from Sigma.

II. Preparation and Composition of M-VDB Medium
With the following ingredients

| | |
|---|---|
| Sodium chloride (NaCl) | 6.77 g |
| D-galactose | 0.80 g |
| Sodium pyruvate | 0.20 g |
| Potassium chloride (KCl) | 0.40 g |
| Magnesium chloride (MgCl$_2$ · 6H$_2$O) | 2.0 g |
| Calcium chloride (CaCl$_2$ · 2H$_2$O) | 0.20 g |
| Sodium dihydrogen phosphate (NaH$_2$PO$_4$ · H$_2$O) | 0.14 g |
| Sodium succinate | 1.0 g |

-continued

| | |
|---|---|
| Succinic acid | 0.75 g |
| L-Glutamine (+) | 0.30 g |
| Amino acids BME 1000 x | 10 ml |
| Vitamins BME 100 x | 10 ml |
| Phenol red stock solution (i.e. 1% phenol red in an aqueous solution of 0.05N NaOH) | 1 ml | a maintenance medium for cell cultures was prepared by dissolving everything in 960 ml distilled water, subsequently adjusting the pH to 7,4 with NaOH (10N) and filtering to sterile through a 0.2μ membrane filter. 2% Newborn Calf Serum (for VERO cells) or 2% foetal calf serum (for other cells) was then added.

Example 2

Antiviral Activity
1. Antiviral activity of the components

In this example use was made of VERO cells which came from the American Type Culture Collection (accession number CCL 26). VERO cells were cultured in Medium 199 (Gibco) with Earle's salts and 5% calf serum. As virus source was used Herpes Simplex Virus 1 (HSV-1, characterized clinical isolate), which was cultured in M-VDB with 100 μg/ml penicillin, 100 μg/ml streptomycin and 2% calf serum.

On a monolayer of VERO cells cultured in microtitre plates (96 wells with flat bottom) was arranged 100 μl of a dilution series of $10^{-1}$ to $10^{-6}$ of HSV-1 in M-VDB. The virus was allowed to adsorb to the cells for 60 to 90 minutes. A dilution series of the test product in M-VDB was then added to the infected cells. In order to check the cytotoxicity of the product the dilutions of the product were likewise added to non-infected cells. After the incubation at 37° C. in a humid chamber for 5 days the cytopathogenic effect (CPE) was evaluated microscopically.

The antiviral activity of the product is expressed as the reduction factor (RF) of the highest non-toxic concentration of the sample. The reduction factor (RF) is the ratio of the concentration of virus in the control compared to the concentration of living virus in the product dilutions. An RF of $\geq 10^2$ is considered significant. The results of the experiment with propyl gallate are shown in table 1.

TABLE 1

| Test product | Test concentration | Reduction factor virus titre |
|---|---|---|
| Propyl gallate dissolved in DMSO and diluted in M-VDB | 100 μg/ml | $10^4$ |
| idem | 50 μg/ml | $10^4$ |
| idem | 25 μg/ml | $10^3$ |
| idem | 10 μg/ml | 1 |

From the above can be seen that the antiviral activity of propyl gallate for HSV-1 is still significant up to a concentration of 25 μg/ml.

The virucidal activity was determined by mixing virus suspensions containing $10^6$ cfu HSV-1 with an equal volume of the test product solutions in different concentrations. This mixture was incubated for a determined time at controlled temperature. A dilution series of $10^{-1}$ to $10^{-6}$ of each mixture was placed on a monolayer of VERO cells. After incubation for five days at 37° C. the CPE was evaluated. The result was expressed in RF. Once again a titre reduction of $\geq 10^2$ was considered significant.

The results of the virucidal activity in respect of HSV-1 at 34° C. for 15 minutes are shown in table 2.

TABLE 2

| Test product | Test concentration | Reduction factor |
|---|---|---|
| Propyl gallate | 500 µg/ml | 1 |
| Cetrimide | 500 µg/ml | $10^5$ |
|  | 250 µg/ml | $10^5$ |
|  | 125 µg/ml | $10^5$ |
|  | 100 µg/ml | $10^5$ |
|  | 50 µg/ml | 10 |
|  | 10 µg/ml | 1 |
| Propyl gallate/Cetrimide (2/1) | 500/250 | $10^5$ |
| Propyl gallate/Cetrimide (2/1) | 250/125 | $10^5$ |

From the above can be seen that propyl gallate displays no virucidal activity and that Cetrimide has virucidal activity up to a concentration of 100 µg/ml. The mixture of propyl gallate and Cetrimide retains its virucidal activity despite an excess of propyl gallate (2/1).

2. Antiviral Properties of the Test Mixture

In similar manner the antiviral activity of the test mixture prepared in example 1 was determined. The results of the virucidal activity of the unguent at 25° C. for 15 minutes are shown in table 3.

Table 3 shows that the unguent still displays virucidal activity in respect of HSV-1 up to a dilution of 1/100 at 25° C. The cetrimide thus retains its full activity, even at 25° C.

TABLE 3

| Test mixture | Dilution | RF |
|---|---|---|
| 93J12 | 1/2 | $10^5$ |
|  | 1/4 | $10^5$ |
|  | 1/8 | $10^5$ |
|  | 1/16 | $10^5$ |
|  | 1/32 | $10^5$ |
|  | 1/64 | $10^5$ |
|  | 1/128 | $10^5$ |
|  | 1/256 | 1 |

Example 3

Antibacterial Activity

The antibacterial activity of the separate components as well as the end product was determined with the test organisms *Candida albicans* (ATTC 10231), *Escherichia coli* (ATTC 8739), *Pseudomonas aeruainosa* (ATTC 15442) and *Staphylococcus aureus* (ATTC 6538). The media used were Tryptic Soy Broth (TSB), Tryptic Soy Agar (TSA) and Sterile Phosphate buffer (PBS).

I. Antibacterial Activity of Components and Mixtures

In order to determine the minimal inhibiting concentration (MIC) an overnight culture was prepared of each microorganism in TSB at 37° C. A 1/2 dilution series was likewise made in TSB of the test products used. 100 µl of each dilution was placed in a microtitre plate. The overnight cultures were diluted 1/1000 in TSB. Of each bacterial suspension 100 µl was likewise added to the product dilutions. As controls for the sterility were used product dilutions without addition of bacteria and bacterial dilutions without addition of product dilutions. The microtitre plates were incubated for 24 hours at 37° C. in a humid chamber. The bacterial growth was evaluated on the basis of the turbidity of the suspension. The MIC value is the lowest product concentration which can prevent the normal growth of a micro-organism, i.e. does not result in any turbidity.

The results are shown in table 4.

TABLE 4

| Test product % | Candida albicans | Escheridia coli | Pseudomonas aeruginosa | Staphylococcus aureus |
|---|---|---|---|---|
| Camomile extract (v/v) | >25% | >25% | >25% | 12,5% |
| Propyl gallate (w/v) | >0,2 % | 0,05% | 0,1% | 0,2% |
| Cetrimide (w/v) | 0,001% | 0,003% | 0,003% | 0,0005% |
| Camomile 10% + Cetrimide 0,5% | — | 1/128 | — | — |
| Camomile 5% + Propyl gallate 0,2% + Cetrimide 0,5% | 1/512 | 1/128 | 1/128 | 1/1024 |

The above shows that the camomile extract has a very limited antibacterial activity in respect of some microorganisms and only in high concentrations. Propyl gallate and cetrimide on the other hand have a significant antibacterial activity. In the mixtures cetrimide is found to retain its antibacterial activity.

II. Antibacterial Activity of the Test Unguent

Three separate portions of unguent were prepared, as described in example 1, which were given the lot numbers 94A12, 94D21 and 94E05. As placebo the same composition was prepared, with omission however of cetrimide. The placebo is designated with 94D27. As control was used 1% cetrimide in sterile distilled water. All test samples were stored at room temperature.

IIa. Determination of minimal inhibiting concentration (MIC).

The minimal inhibiting concentration is that concentration of the test product below which bacteria will no longer grow. The highest test concentration used (1/10 dilution) was prepared by suspending one gram of unguent in 9 ml sterile distilled water. The dilutions were added to the bacteria, which were then cultured for 24 hours. The used test organisms were *Candida albicans* (Ca), in a quantity of $10^5$, $10^6$ *Escherichia coli* (Ec), $10^5$ *Pseudomonas aeruginosa* (Pa), and $10^6$ *Staphylococcus aureus* (Sa).

Table 5 shows the dilution in which the growth of bacteria is inhibited.

TABLE 5

| Test Mixture | Ca | Ec | Pa | Sa |
|---|---|---|---|---|
| 94A12 | 1/80 | 1/160 | 1/40 | 1/5120 |
| 94D21 | 1/80 | 1/160 | 1/40 | 1/5120 |
| 94D27 | >1/20 | >1/20 | >1/20 | >1/20 |
| 94E05 | 1/80 | 1/160 | 1/40 | 1/5120 |
| Cetrimide 1% | 1/80 | 1/320 | 1/40 | 1/5120 |

The table shows that all test unguents retain their antibacterial activities. The MIC of these unguents is comparable to the MIC value of 1% cetrimide in water. In the tested concentrations the placebo has no antibacterial activity.

IIb. Determination of the bactericidal and fungicidal activity

The bactericidal activity is tested with *Candida albicans* ($10^5$), *Escherichia coli* ($10^6$), *Pseudomonas aeruginosa* ($10^5$) and *Staphylococcus aureus* ($10^6$). The bactericidal activity is determined in accordance with the specifications of the European Pharmacopeia. These entail the product for testing being mixed with the micro-organism and incubated for a time, whereafter this mixture is diluted and it is determined at which of the dilutions growth of bacteria still occurs.

A dilution was prepared of each micro-organism up to an end concentration of $10^6$–$10^7$ cfu. The unguents are tested undiluted and in a 1/2 and 1/10 dilution in sterile distilled water. To one gram of the unguent or its dilution 100 µl of a diluted inoculum was added and mixed. After 15 minutes incubation at 25° C. a 1/10 dilution series was prepared in TSB (Tryptic Soy Broth (Gibco)) from 100 mg of this mixture. Each dilution was plated out on TSA (Tryptic Soy Agar (Gibco)). The plates were incubated for 24 hours at 37° C. As controls were used an untreated culture of the micro-organisms and 1% cetrimide in distilled water activity. After incubation all plates were evaluated for growth. The tests expressed in Reduction factor (Rf) were performed three times. The results are shown in table 6.

TABLE 6

| Test mixture | | Ca($10^6$) | Ec($10^6$) | Pa($10^5$) | Sa($10^5$) |
|---|---|---|---|---|---|
| 94A12 | 1/1 | $-10^5$ | $-10^6$ | $-10^5$ | $-10^6$ |
| | 1/2 | $-10^5$ | $-10^6$ | $-10^5$ | $-10^6$ |
| | 1/10 | $-10^5$ | $-10^6$ | $-10^5$ | $-10^6$ |
| 94D21 | 1/1 | $-10^5$ | $-10^6$ | $-10^5$ | $-10^6$ |
| | 1/2 | $-10^5$ | $-10^6$ | $-10^5$ | $-10^6$ |
| | 1/10 | $-10^5$ | $-10^6$ | $-10^5$ | $-10^6$ |
| 94D27 | 1/1 | $-10^5$ | $-10^3$ | 1 | $-10$ |
| | 1/2 | $-10^5$ | $-10^3$ | 1 | $-10$ |
| | 1/10 | $-1$ | $-1$ | 1 | 1 |
| 94E05 | 1/1 | $-10^5$ | $-10^6$ | $-10^5$ | $-10^6$ |
| | 1/2 | $-10^5$ | $-10^6$ | $-10^5$ | $-10^6$ |
| | 1/10 | $-10^5$ | $-10^6$ | $-10^5$ | $-10^6$ |
| Cet 1% | 1/1 | $-10^5$ | $-10^6$ | $-10^5$ | $-10^6$ |
| | 1/2 | | | | |
| | 1/10 | $-10^5$ | $-10^6$ | $-10^5$ | $-10^6$ |

The table above shows that all test unguents also retain their bactericidal activity in dilutions. All bacteria were killed. The placebo was found to have a very limited bactericidal activity.

IIc. Funaicidal activity

In order to determine the fungicidal activity test organisms *Epidermophyton floccosum* (RV 69635) and *Trichophyton rubrum* (RV58124) were used.

The fungicidal activity was determined in the same manner as the bactericidal activity.

For this purpose a dilution was prepared of each micro-organism up to an end concentration of $10^4$–$10^5$ cfu. The unguents were tested undiluted and in a 1/2 and 1/10 dilution in sterile distilled water. To one gram of the unguent or its dilution 100 µl of a diluted inoculum was added and mixed. After 15 minutes incubation at 25° C. a 1/10 dilution series was prepared in SAB (Sabouraud Bouillon (Gibco)) from 100 mg of this mixture. Each dilution was plated out on SABA (Sabouraud Agar (Gibco)). The plates were incubated for 5 days at 25° C. As controls were used an untreated culture of the micro-organisms and 1% cetrimide in distilled water. After incubation all plates were evaluated for growth. The tests were performed three times. The results, expressed in Reduction factor (Rf), are shown in table 7.

TABLE 7

| Test Mixture | Epidermophyton floccosum ($10^3$) | Trichophyton rubrum ($10^4$) |
|---|---|---|
| 94A12 | $10^2$ | $10^4$ |
| 94D21 | $10^2$ | $10^4$ |
| 94D27 | 10 | $10^2$ |
| 94E05 | $10^2$ | $10^4$ |
| Cetrimide 1% | $10^2$ | $10^4$ |

The table above shows that the test unguents retain their fungicidal activity, which is comparable to that of 1% cetrimide in distilled water. The placebo has a limited fungicidal activity.

IId. Virucidal activity

The virucidal activity was determined according to the micro-method described by D. Vanden Berghe et al. in "Methods in Plant Biochemistry", Vol. 6 "Assays for Bioactivity", p. 49–67, Academic Press Limited 1991. To 300 µl product dilutions was added 300 µl undiluted virus suspension. These mixtures were incubated for 15' at 34° C. Dilution tubes were provided with 0.9 ml cooled culture medium for virus and placed in an ice bath. 100 µl of the incubated mixtures was placed in the dilution tubes. A 1/10 dilution series was prepared therefrom. 200 µl of these dilutions was placed on the VERO cells. Controls were untreated virus (=virus control) and untreated cells (=cell control). The plates were incubated at 37° C. in a humid incubator for 5 to 7 days. The cells were evaluated microscopically for cytotoxic and cytopathogenic effect (CPE). The results are expressed in Reduction factor (Rf). The reduction factor is the ratio of the concentration of residual virus to the initial virus concentration. The tests were performed three times. The results expressed in Rf are shown in table 8.

TABLE 8

| Test mixture | 1/2 | 1/5 | 1/10 | 1/20 | 1/50 |
|---|---|---|---|---|---|
| 94A12 | $10^5$ | $10^5$ | $10^5$ | $10^5$ | $10^5$ |
| 94D21 | $10^5$ | $10^5$ | $10^5$ | $10^5$ | $10^5$ |
| 94D27 | 1 | 1 | 1 | 1 | 1 |
| 94E05 | $10^5$ | $10^5$ | $10^5$ | $10^5$ | $10^5$ |
| Cetrimide 1% | $10^5$ | $10^5$ | $10^5$ | $10^5$ | $10^5$ |

The table above shows that the test unguents have a virucidal activity up to the dilution 1/50. The virucidal activity is comparable to the activity of 1% cetrimide. The placebo has no virucidal activity.

Example 4

In vivo Activity Test

The test group consisted of fifteen patients with cold sores on their lips. They were treated with an unguent with the following composition:

| | |
|---|---|
| PEG 400 | 52% |
| PEG 4000 | 26% |
| glycerol | 9% |
| cetrimide | 1% |
| choline (optional) | 2% |
| cetyl alcohol | 1% |
| camomile extract | 8% |
| propyl gallate | 0.25% |

The results of the experiment are given in the following table 9.

TABLE 9

CLINICAL EVALUATION OF ANTI-HSV ACTIVITY OF THE TEST UNGUENT IN VIVO

| Patient | Treatment frequency | Treatment duration | Result effect | which effect | side-effects | earlier treatment | Remarks |
|---|---|---|---|---|---|---|---|
| 1 | 3x/day | 1 day | yes | blisters do not develop | no | Zovirax | used at first tingling |
| 2 | 2x/day | 1 day | yes | no spreading/ rapid healing | tingling | Zovirax | — |
| 3 | 4–5x /day | 3 days | yes | rapid heating | no | Pâte hima | — |
| 4 | 6/day | 7 days | yes | blisters dry faster than previously | no | Zovirax | — |
| 5 | 4–5/day | 3 day | yes | rapid healing | no | Zovirax | tastes bad |
| 6 | 5/day | 4–6 days | yes | quick recovery | no | Zovirax | — |
| 7 | 2/day | 2 days | yes | blisters do not develop | no | unknown | used preventively in case of cold |
| 8 | 2/day | 3 days | yes | rapid heating | yes: drying out | unknown | no further repetition of symptoms later/used to be > 1x per month |
| 9 | 3/day | 4 days | yes | quick recovery | no | unknown | less frequent repetition of symptoms later/no more in four months |
| 10 | 1/day | 30 days | yes | no repetition of symptoms in 12 months | no | unknown | frequency used to be >1x per month |
| 11 | 2/day | 4–5 days | yes | rapid healing | no | vaseline | less frequent repetition of symptoms |
| 12 | 2–3/day | 4 days | yes | rapid healing | no | Zovirax | — |
| 13 | 3/day | 4 days | yes | rapid healing/ no spreading | no | Zovirax | less frequent repetition of symptoms |
| 14 | 2/day | 3 days | yes | rapid healing/ no spreading | no | Zovirax | less frequent repetition of symptoms |
| 15 | 3/day | 4 days | yes | rapid healing/ no spreading | no | Zovirax | If used preventively in case of cold; at first tingling → no outbreak |

In a second experiment with 2 male patients the preventive action of the unguent was tested. To this end the unguent was applied once a day for six months at the location where normally speaking lesions occurred. The result of this treatment was that repetitions of the symptoms no longer occurred, even in cases of colds. Prior to the treatment one of the two patients had cold sores at least once a month, while in both patients colds were always accompanied by symptoms.

The present invention provides a new pharmaceutical composition for the treatment of herpes infections, in particular facial or labial herpes caused by HSV-1 or -2. The great difference from other remedies is that most patients who use the remedy curatively or preventively no longer have repetitions of the symptoms later in the same location.

What is claimed is:

1. A pharmaceutical composition for the treatment of herpes simplex infections, comprising a quaternary ammonium compound in a concentration effective to exhibit virucidal activity against herpes simplex virus, an antiviral agent and a pharmaceutically acceptable base, wherein the quaternary ammonium compound is present in a range from about 0.1% to about 5% and is selected from the group consisting of cetrimide and a benzalkonium compound; and the antiviral agent is present in a range from about 0.01% to about 3% and is selected from the group consisting of an acyclovir, bromylvinyldesoxuridine, 3-fluorothymidine, idoxuridine, propyl gallate, ethyl gallate, proanthocyanides and glucosamine, wherein the quaternary ammonium compound and the antiviral agent are mutually compatible.

2. The pharmaceutical composition of claim 1, further comprising a plant extract present in a range from above 0% to about 20%.

3. The pharmaceutical compound of claim 2, wherein the plant extract is selected form the group consisting of *Aesculus hippocastanum* L; *Aloe vera* L; *Anagallis arvensis* L; *Anthemis nobilis* L; *Arctium lappa* L; *Aristolochia clematitis* L; *Arnica montana* L; *Betonica officinalis* L; *Calendula officinalis* L; *Capsicum annuum* (*tetragonum*); *Carica papaya* L; *Carlina acaulis* L; *Caryophyllus aromaticus* L; *Cynoglossum officinale* L; *Echinacea augustifolia; Echinacea purpurea* L; *Eupatorium cannabinum* L; *Geranium robertianum; Geum urbanum* L; *Glechoma hederacea* L; *Hamamelis virginiana* L; *Hypericum perforatum* L; *Inula helenium* L; *Juglans regia* L; *Juniperus oxycedrus* L: *Lavandula officinalis; Lawsonia alba* L; *Lysimachia nummeralia* L: *Lythrum salicaria* L: *Malva sylvestris; Marrubium vulgare* L; *Matricaria chamomilla* L; *Mentha piperita* L; *Myroxylon balsamum* L; *Myrtus communis* L; *Olea europaea* L; *Prunus amygdalus; Pyrus cydonia* L; *Quercus robur* L; *Quillaja saponaria; Rubus idaeus* L; *Salvia officinalis* L; *Saponaria officineals* L; *Smilax officinalis; Solanum dulcamara* L; *Solidago virga aurea* L; *Styrax tonkinensis; Styrax benzoides; Styrax benzoin; Symphytum officinale* L; *Trigonella foenum-graecum* L; *Tropaeolum majus* L; *Urtica urens* L; *Urtica dioica* L; and *Viola tricolor* L.

4. The pharmaceutical composition of claim 2, wherein the plant extract is present in a range from about 1% to about 20%.

5. The pharmaceutical composition as claimed in claim 1, wherein the quaternary ammonium compound is cetrimide.

6. The pharmaceutical composition as claimed in claim 1, wherein the quaternary ammonium compound is benzalkoniun chloride.

7. The pharmaceutical composition as claimed in claim 2, wherein the plant extract is selected from the group consisting of extracts of camomile, calendula, sage, great burdock, and senna and the quaternary ammonium compound is cetrimide.

8. The pharmaceutical composition as claimed in claim 2, wherein the plant extract is selected from the group consisting of extracts of camomile, calendula and senna and the quaternary ammonium compound is benzalkonium chloride.

9. A pharmaceutical composition for the treatment of herpes simplex virus infections, comprising:

| | |
|---|---|
| PEG 400 | 52% |
| PEG 4000 | 26% |
| glycerol | 9% |
| cetrimide | 1% |
| choline (optional) | 2% |
| cetyl alcohol | 1% |
| camomile extract | 8% |
| propyl gallate | 0.25% |

10. A method for the treatment of herpes simplex infections, comprising administration of a pharmaceutical composition comprising a quaternary ammonium compound in a concentration effective to exhibit virucidal activity against herpes simplex virus, an antiviral agent, and a pharmaceutically acceptable base, wherein the quaternary ammonium compound and the antiviral agent are mutually compatible, the quaternary ammonium compound is present in a range about 0.1 to about 5% and is selected from the group consisting of cetrimide and a benzalkonium compound, the antiviral agent is present in a range from about 0.01 to about 3% and is selected from the group consisting of an acyclovir, bromoinyldesoxuridine, 3-fluorothymidine, idoxuridine, propyl gallate, ethyl gallate, proanthocyanides and glucosamine.

* * * * *

UNITED STATES PATENT AND TRADEMARK OFFICE
CERTIFICATE OF CORRECTION

PATENT NO. : 6,284,289 B1
DATED : September 4, 2001
INVENTOR(S) : Dirk Andre Richard Van Den Berghe It is certified that error appears in the above-identified patent and that said Letters Patent is hereby corrected as shown below:

Title page,
Item [56], References Cited, OTHER PUBLICATIONS,
Refer to Colgate reference, line 2, "Activiey" should read -- Activity --.

Column 4,
Line 21, "*amyadalus*" should read -- *amygdalus* --.

Column 7,
Line 48, "*aeruainosa*" should read -- *aeruginosa* --.

Column 9,
Line 36, heading: "Funaicidal" should read -- Fungicidal --.

Column 11-12,
Table 9, under "Result" column, subheading "which effect", refer to "Patient 3": "rapid heating" should read -- rapid healing --; and under "Result" column, subheading "which effect", refer to "Patient 8": "rapid heating" should read -- rapid healing --.

Column 12, claim 3,
Line 44, "*officineals*" should read -- *officinalis* --.

Signed and Sealed this

Nineteenth Day of March, 2002

JAMES E. ROGAN
Director of the United States Patent and Trademark Office